United States Patent
Gopalakrishnan et al.

(10) Patent No.: US 9,205,278 B2
(45) Date of Patent: Dec. 8, 2015

(54) METHOD OF PROVIDING UNIFORM DISTRIBUTION OF LIGHT IN A PHOTOTHERAPY DEVICE

(75) Inventors: Satish Kumar Gopalakrishnan, Bangalore (IN); Sirosh Sivasankaran, Bangalore (IN); Mohammed Yousuf Ali Imran, Bangalore (IN); Manickalinga Soruban Thandapani, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 730 days.

(21) Appl. No.: 13/469,811

(22) Filed: May 11, 2012

(65) Prior Publication Data

US 2013/0030264 A1    Jan. 31, 2013

(30) Foreign Application Priority Data

May 13, 2011    (IN) .......................... 1645/CHE/2011

(51) Int. Cl.
*A61N 5/06* (2006.01)
*H05B 33/08* (2006.01)

(52) U.S. Cl.
CPC .......... *A61N 5/0621* (2013.01); *H05B 33/0851* (2013.01); *A61N 2005/0628* (2013.01); *A61N 2005/0652* (2013.01)

(58) Field of Classification Search
CPC ................................ A61B 5/00; A61B 5/0059
USPC .......................................... 600/407, 473, 476
See application file for complete search history.

(56) References Cited

U.S. PATENT DOCUMENTS

2007/0016078 A1*    1/2007   Hoyt et al. ................... 600/476

* cited by examiner

*Primary Examiner* — Peter Luong
(74) *Attorney, Agent, or Firm* — GE Global Patent Operation; Marc A. Vivenzio

(57) ABSTRACT

A method of computing peak spectral irradiance, the method comprising characterizing at least one light source to determine an irradiance distribution pattern, generating multiple density cones in a three dimensional model based on the irradiance distribution pattern, positioning the multiple density cones in a desired layout, measuring density of irradiance at one or more locations, and optimizing the positioning of the at least one light source to obtain a desired irradiance distribution.

9 Claims, 5 Drawing Sheets

200

METHOD OF PROVIDING UNIFORM DISTRIBUTION OF LIGHT IN A PHOTOTHERAPY DEVICE

BACKGROUND OF THE INVENTION

1. Field of the Invention

Embodiments of the present invention generally relate to a phototherapy device and, more particularly, to methods of providing uniform distribution of light in a phototherapy device.

2. Description of the Prior Art

Phototherapy is a promising clinical tool for the treatment of many conditions, including seasonal affective disorder, bulimia nervosa, herpes, psoriasis, sleep disorders, acne, and skin cancer.

Phototherapy is especially promising as a treatment for hyperbilirubinemia, a common condition affecting 70% of all full-term infants. Hyperbilirubinemia is caused by the accumulation of excess bilirubin in the blood and skin of the infant. This excess bilirubin turns the skin and sclera a characteristic yellow color. If left untreated, extreme cases of hyperbilirubinemia can result in neurological insult (kernicterus) or even death. A common treatment for hyperbilirubinemia is phototherapy, in which the infant is exposed to light in a range corresponding to the peak absorption spectra for bilirubin (blue-green 0-520 nm). This light changes the form of the bilirubin to a different isomer that is more readily eliminated by the body.

A number of different light sources can be used for phototherapy. Traditionally, broadband sources have been used, such as fluorescent, halogen, or incandescent light. However, it has been recently suggested that light-emitting diodes (LEDs) can be an effective phototherapeutic light source.

When using LEDs, multiple devices may be necessary to ensure proper surface area coverage. When using banks of LEDs, caregivers must ensure that the intensity delivered to the entire surface area is within the effective intensity range. The international standards governing phototherapy systems, state that peripheral intensity must equal or exceed 40 percentage of the peak intensity. When measuring the irradiance, caregivers should take measurements at multiple points along the treatment area to verify that their device meets these standards.

The current method used for optimizing the type of LED, number of LEDs and location of LEDs for achieving peak irradiance and desired spectral irradiance distribution involves physical testing, which is time consuming.

Therefore, towards improving the application of effective phototherapy, there is a need to develop an efficient, reliable and user-friendly method of optimizing the positioning of LEDs for achieving peak irradiance and uniform spectral irradiance distribution.

BRIEF SUMMARY OF THE INVENTION

According to an embodiment of the present invention, there is provided a method of computing peak spectral irradiance. The method comprises characterizing at least one light source to determine an irradiance distribution pattern, generating multiple density cones in a three dimensional model based on the irradiance distribution pattern, positioning the multiple density cones in a desired layout, measuring density of irradiance at one or more locations, and optimizing the positioning of the at least one light source to obtain a desired irradiance distribution.

According to another embodiment of the present invention, there is provided an illumination system. The illumination system comprises at least one light source configured to emit illumination light, a sensor configured to detect the illumination light emitted from the at least one light source and to transmit a signal representing the irradiance distribution of the illumination light, a processor configured to receive the signal from the sensor, to characterize an irradiance distribution pattern of the at least one light source based on the signal received, to generate a plurality of density cones in a three dimensional model based on the irradiance distribution pattern, and to measure density of irradiance at one or more locations, and a controller coupled to the processor, wherein the controller is configured to optimize the positioning of the at least one light source to obtain a desired irradiance distribution.

According to another embodiment of the present invention, there is provided a method of illuminating tissue for at least one of phototherapy, photodynamic therapy or diagnosis. The method comprises generating an illumination light using at least one light source, detecting the illumination light and transmitting data corresponding to the illumination light using a sensor, analyzing an irradiance distribution pattern of the at least one light source based on the data received to optimize the positioning of the at least one light source and to obtain a desired irradiance distribution, and directing illumination light comprising the desired irradiance distribution toward a target tissue.

According to another embodiment of the present invention, there is provided a computer controlled illumination system. The system comprises at least one light source configured to emit illumination light, a sensor configured to detect the illumination light and transmit data corresponding to the illumination light, and a controller configured to analyze an irradiance distribution pattern of the at least one light source based on the data received, and to optimize the positioning of the at least one light source to obtain a desired irradiance distribution.

According to another embodiment of the present invention, there is provided a computer controlled radiation system. The system comprises at least one radiation source configured to emit radiation, a sensor configured to detect the radiation and transmit data corresponding to the radiation, and a controller configured to analyze a radiance distribution pattern of the at least one radiation source based on the data received, and to optimize the positioning of the at least one radiation source to obtain a desired radiance distribution.

BRIEF DESCRIPTION OF THE DRAWINGS

Systems and methods of varying scope are described herein. In addition to the aspects and advantages described in this summary, further aspects and advantages will become apparent by reference to the drawings and with reference to the detailed description that follows, wherein.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
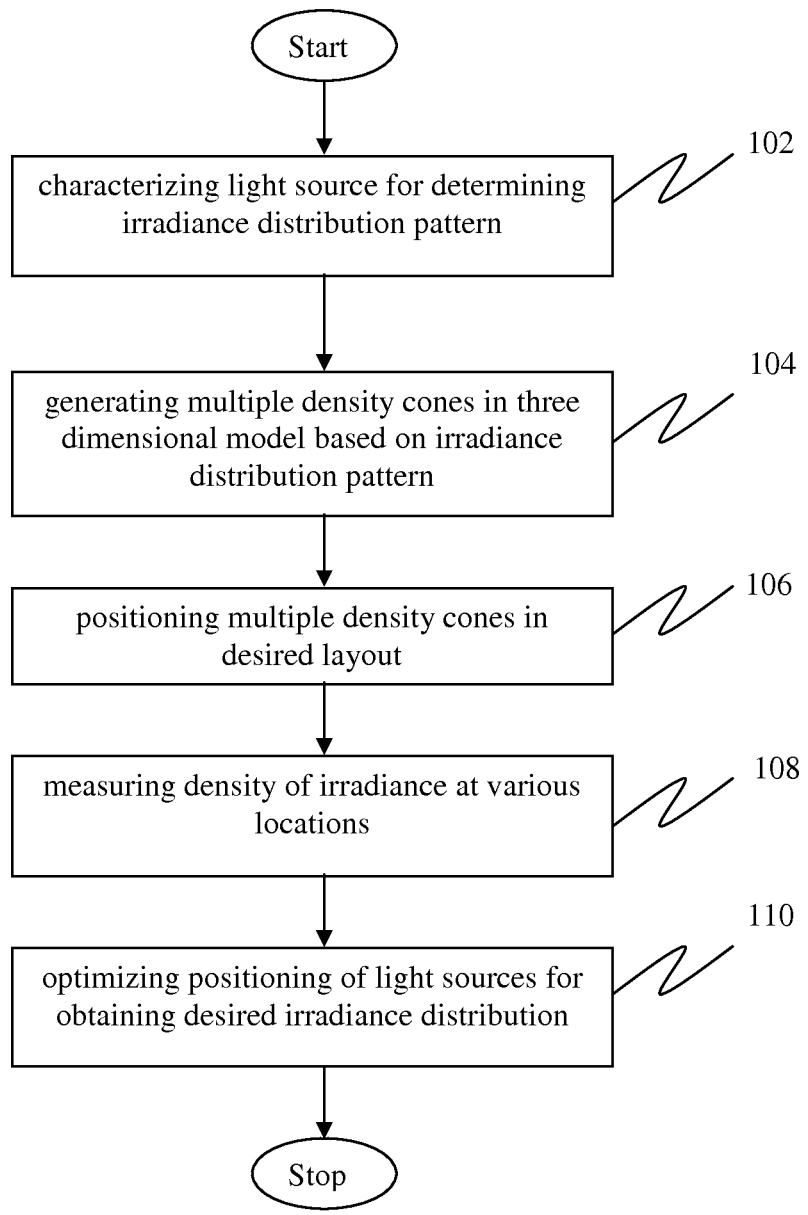
FIG. 1 shows a flow diagram depicting a method of computing peak spectral irradiance according to an embodiment of the present invention.

Embodiments of the present invention provide several methods and systems for achieving desired spectral irradiance distribution in an illumination system that is used for phototherapy, photodynamic therapy and diagnosis. Accordingly, in one embodiment, as shown in FIG. 1, a method 100 of computing peak spectral irradiance is provided. The method 100 comprises steps of characterizing a light source for determining irradiance distribution pattern at step 102, generating multiple density cones in a three dimensional model based on the irradiance distribution pattern at step 104, positioning the multiple density cones in a desired layout at step 106, measuring density of irradiance at one or more locations at step 108 and optimizing the position of one or more light sources for obtaining desired irradiance distribution at step 110.

The light intensity emitted by a light source is measured at several points in a predetermined area of illumination. Intensity, measured as microwatts per square centimeter per nanometer ($\mu W/cm^2/nm$), is dependent upon the power of the light source and the distance of the point where the intensity is measured from the light source. The intensity of the light source is inversely related to the distance of the measuring point from the light source. Although peak intensity, typically in the center of the light, may be considered "intensive", it may not represent the intensity incident on a patient's entire body.

Further, each light source is characterized by determining the irradiance distribution pattern. Multiple density cones are generated in a three dimensional model based on the irradiance distribution pattern. The density cones thus generated are positioned in a desired layout. The combined density of irradiance is measured at one or more locations. Subsequent to the irradiance measurement, positioning of one or more light sources is manipulated and further optimized for obtaining desired irradiance distribution in a predetermined illumination area.

Figure 2:
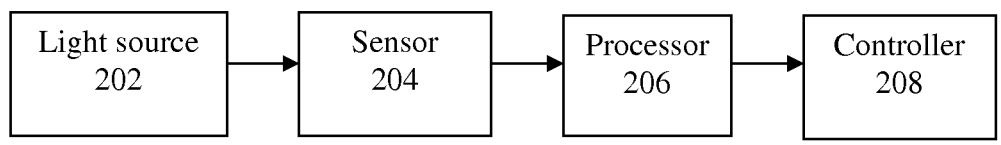
FIG. 2 shows a block diagram depicting an illumination system according to an embodiment of the present invention.

In another embodiment, as shown in FIG. 2, an illumination system 200 configured for performing the method 100 is described. The illumination system 200 comprises at least one light source 202 configured to emit illumination light, a sensor 204 configured to detect the light emanating from the light source 202 and transmit a signal representing the irradiance distribution of the emanated light, a processor 206 configured for receiving and processing the signal from the sensor 204 and a controller 208 coupled to the processor 206 for optimizing the positioning of one or more light sources 202 for obtaining desired irradiance distribution. Further, the processor 206 is configured for characterizing the irradiance distribution pattern of the light source 202 based on the signal received, generating multiple density cones in a three dimensional model based on the irradiance distribution pattern, positioning the multiple density cones in a desired layout and for measuring density of irradiance at one or more locations.

In one embodiment, the illumination system 200 comprises one of a phototherapy device, a photodynamic therapy device and/or a diagnosis device. Further, the light source 202 comprises one of a light emitting diode, fluorescent bulb, filament based bulb, an LED lamp, an optical spectral filter, an LED lamp and phosphor converters, and semiconductor nanocrystal photonic converters. Accordingly, the illumination light comprises one of an ultraviolet (UV) light, blue light, visible light, near-infrared (NIR) light and infrared (IR) light.

The LED typically has a bell shaped curve for the chart of relative spectral irradiance. Each of the one or more light sources 202 is assumed to have equal mean irradiance, rate of decay of irradiance, and treatable surface area of the footprint of light.

The illumination system 200 may further comprise an optical filter (not shown) capable of distributing the light in a spatially consistent manner including, but not limited to, a diffuser, a lens, and a collimator.

Figure 3:
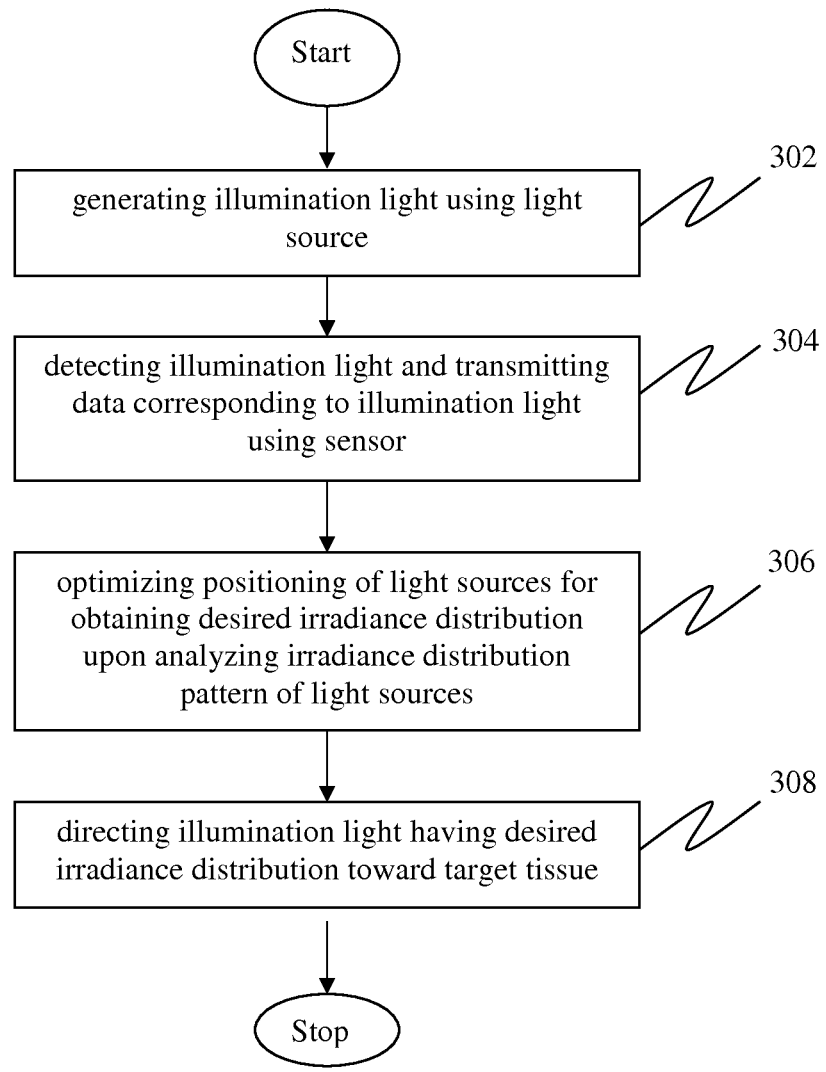
FIG. 3 shows a flow diagram depicting a method of illuminating a tissue structure according to an embodiment of the present invention.

In another embodiment, as shown in FIG. 3, a method 300 of illuminating tissue for at least one of phototherapy, photodynamic therapy or diagnosis is provided. The method 300 comprises steps of generating an illumination light using a light source at step 302, detecting the illumination light and transmitting data corresponding to the illumination light using a sensor at step 304, analyzing irradiance distribution pattern of the light source based on the data received to optimize the positioning of one or more light sources for obtaining desired irradiance distribution at step 306 and directing the illumination light having desired irradiance distribution toward a target tissue at step 308.

In another embodiment, a computer-controlled illumination system is described that one may use to generate light for diagnostic or therapeutic interventions. For example, the computer-controlled illumination system may be used for phototherapy in which one or more tissues such as skin, muscle and internal organs, etc. are illuminated with light, or photodynamic therapy in which a drug or some other chemical is introduced into one or more tissues and activated by light, or diagnosis in which the presence of a drug or some other chemical in one or more tissues is revealed.

Figure 4:
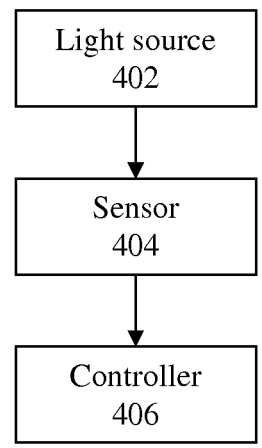
FIG. 4 shows a block diagram depicting a computer controlled illumination system according to an embodiment of the present invention.

FIG. 4 provides a schematic depiction of the computer-controlled illumination system 400 as described in an embodiment of the present invention. The computer-controlled illumination system 400 generates and emits an illumination light having a selected spectral output and a selected wavelength dependent intensity distribution that may be directed to tissue for at least one of the following: phototherapeutic procedures, photodynamic procedures and diagnostic procedures. Furthermore, one may easily vary the spectral output and a selected wavelength dependent intensity distribution of the illumination light as desired to correspond with different procedures or different conditions within the same procedure. The computer-controlled illumination system 400 as shown comprises a light source 402 configured to emit the illumination light, a sensor 404 configured to detect the illumination light and transmit data corresponding to the illumination light and a controller 406 configured to analyze irradiance distribution pattern of the light source 402 based on the data received to optimize the positioning of one or more light sources 402 for obtaining desired irradiance distribution.

The sensor 404 transmits the data representing the spectral intensity or peak spectral irradiance distribution to the controller 406 and may be any desired device capable of sensing the illumination light and generating data representing the spectral distribution of the illumination light. For example, the sensor 404 may comprise spectrometers, spectroradiometers, charge-coupled devices (CCDs), charge injection devices (CIDs), a complementary metal-oxide semi-conductors (CMOSs), photodiode arrays. In some embodiments, the sensor 404 receives illumination light from a beam splitter such as lens so that the illumination light projected toward the tissue is not affected by the sensor 404.

The controller 406 receives the data representing the spectral intensity distribution from the sensor 404 and includes computer-implemented programming to coordinate the light source 402, and the sensor 404. Such coordination typically comprise analyzing the irradiance distribution pattern of the light source 402 based on the data received in order to optimize the positioning of one or more light sources 402 for obtaining desired irradiance distribution.

The controller 406 contains or is linked to computer-implemented programming. Typically, the controller 406 comprises one or more computers or other devices comprising a central processing unit (CPU) and directs other devices to perform certain functions or actions. A computer comprises an electronic device that can store coded data and can be set or programmed to perform mathematical or logical operations at high speed. Controllers are well known and selection of a desirable controller for a particular aspect of the illumination system 400 and method 300 described is within the scope of the art.

The computer-controlled illumination system 400 may include other components as desired. For example, the computer-controlled illumination system 400 may comprise at least one of the following: a projection system (not shown) to project the illumination light toward the tissue. The projection system may be desirable to enlarge, decrease or change the geometric form of the coverage area of the illumination light on the tissue area and may comprise any desired optical device to accomplish this. For example, the projection system may include lenses and may focus the illumination light onto an area of the tissue that corresponds to the form of a region of the tissue that is to be illuminated.

In one embodiment, the computer-controlled illumination system 400 is disposed in the proximal end of an illumination-light guide of an endoscope system. The computer-controlled illumination system 400 emits illumination light that is directed into the illumination-light guide. The illumination light is conducted through the endoscope through the illumination light guide to the distal end of the endoscope body where it exits the endoscope system and illuminates the tissue.

In other embodiments, the computer-controlled illumination system 400 may be incorporated in or attachable to endoscopes, surgical microscopes or other optical apparatus such as otoscopes, optical fibers, fiber bundles, liquid light guides and similar devices, to provide illumination light to tissues or other material located in otherwise difficult to reach locations.

In one embodiment, the controller 406 may be located at a remote location from the sensor 404. Transmission of the data from the sensor 404 to the controller 406 may be effected by electrical signals traveling through conducting wires, optical signals traveling through optical fibers or other optical transmission methods or it may be transmitted by wireless communication means such as radio waves or other types of wireless devices or networks, or otherwise as desired.

The controller 406 processes the received data from the sensor 404 to analyze the irradiance distribution pattern of the light source 402. The controller 406 further optimizes the positioning of one or more light sources 402 for obtaining desired irradiance distribution within a predetermined treatable surface area. The controller 406 in the process of analyzing the irradiance distribution pattern may process the data to generate multiple density cones in a three dimensional model, position the multiple density cones in a desired layout and measure density of irradiance at one or more locations. Furthermore, the controller 406 may use the processed data to optimize the positioning of one or more light sources 402 in order to control the illumination light generated by the computer-controlled illumination system 400.

Figure 5:
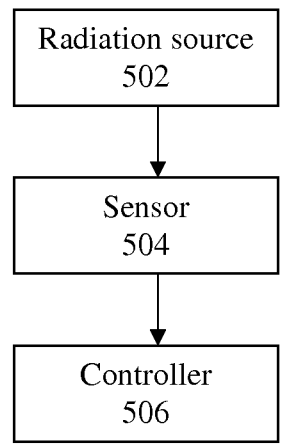
FIG. 5 shows a block diagram depicting a computer controlled radiation system according to an embodiment of the present invention.

In yet another embodiment, as shown in FIG. 5, a computer controlled radiation system 500 comprising a radiation source 502 configured to emit radiation, a sensor 504 configured to detect the radiation and transmit data corresponding to the radiation distribution and a controller 506 configured to analyze radiance distribution pattern of the radiation source 502 based on the data received in order to optimize the positioning of one or more radiation sources 502 for obtaining desired radiance distribution is provided.

The radiation-emitting source comprises combinations of a flexible array of LEDs, fluorescent bulbs, filament based bulbs, an LED lamp, an optical spectral filter, an LED lamp and phosphor converters, and semiconductor nanocrystal photonic converters. Further, the radiation comprises a combination of one or more electromagnetic radiation types including, but not limited to, light, visible light, invisible light, ultraviolet, infrared, radiofrequency, x-ray, and microwave.

In various embodiments of the present invention, a method of computing peak spectral irradiance and thereby achieving uniform distribution of light in a phototherapy device is provided. However, the embodiments are not limited and may be implemented in connection with different applications. The application of these embodiments of the present invention can be extended to other areas, for example, illumination, heating or any such device configured for uniform distribution of a parameter that inversely varies with the distance. Embodiments of the present invention provide a broad concept of achieving uniform distribution of spatially varying parameter, which can be adapted in a similar illumination and/or acoustic and/or telecommunication and/or communication system. The design can be carried further and implemented in various forms and specifications.

The arrangement of LEDs using the illumination system and method described herein ensures uniform treatment dosage across the entire surface area of the illumination.

Uniform irradiation in phototherapy treatments will degrade bilirubin to safe levels faster resulting in shorter treatment times. Thus, effective phototherapy will yield a greater response over a given time interval for better results.

This written description uses examples to describe the subject matter herein, including the best mode, and also to enable any person skilled in the art to make and use the subject matter. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. An illumination system comprising:
at least one light source configured to emit illumination light;

a sensor configured to detect the illumination light emitted from the at least one light source and to transmit a signal representing the irradiance distribution of the illumination light;

a processor configured to receive the signal from the sensor, to characterize an irradiance distribution pattern of the at least one light source based on the signal received, to generate a plurality of density cones in a three dimensional model based on the irradiance distribution pattern, and to measure density of irradiance at one or more locations; and a controller coupled to the processor, wherein the controller is configured to optimize the positioning of the at least one light source to obtain a desired irradiance distribution.

2. The illumination system according to claim 1, wherein the at least one light source comprises one of a light emitting diode, fluorescent bulb, filament based bulb, an LED lamp, an optical spectral filter, an LED lamp and phosphor converters, and semiconductor nanocrystal photonic converters.

3. The illumination system according to claim 1, further comprising at least one of a phototherapy device, a photodynamic therapy device and a diagnosis device.

4. The illumination system according to claim 1, further comprising an optic filter operably configured to distribute illumination light in a spatially consistent manner.

5. The illumination system according to claim 1, wherein the illumination light comprises one of an ultraviolet (UV) light, blue light, visible light, near-infrared (NIR) light and infrared (IR) light.

6. A method for computing peak spectral irradiance to achieve uniform distribution using density cones for LED phototherapy devices, the method comprising:

generating an illumination light using at least one light source;

detecting the illumination light emitted from the at least one light source with a sensor;

transmitting a signal representing the irradiance distribution of the illumination light to a processor;

determining, via the processor, an irradiance distribution pattern of the at least one light source based on the signal received;

generating, via the processor, a plurality of density cones in a three dimensional model based on the irradiance distribution pattern;

measuring, via the processor, a density of irradiance at one or more locations; and optimizing, via a controller in communication with the processor, the positioning of the at least one light source to obtain a desired irradiance distribution.

7. The method according to claim 6, wherein the illumination light comprises one of an ultraviolet (UV) light, blue light, visible light, near-infrared (NIR) light and infrared (IR) light.

8. The method according to claim 6, wherein the at least one light source comprises one of a light emitting diode, fluorescent bulb, filament based bulb, an LED lamp, an optical spectral filter, an LED lamp and phosphor converters, and semiconductor nanocrystal photonic converters.

9. The method according to claim 6, further comprising distributing the illumination light in a spatially consistent manner using an optic filter.

* * * * *